United States Patent
Hauan

(10) Patent No.: US 6,645,473 B2
(45) Date of Patent: Nov. 11, 2003

(54) COMBINATION TANNING AND ANTIFUNGAL TOPICAL SYSTEM FOR TREATING TINEA VERSICOLOR

(76) Inventor: Diana L. Hauan, 102 Friar Dr., Clarksville, TN (US) 37042

(*) Notice: Subject to any disclaimer, the term of this patent is extended or adjusted under 35 U.S.C. 154(b) by 4 days.

(21) Appl. No.: 09/912,284

(22) Filed: Jul. 24, 2001

(65) Prior Publication Data

US 2002/0009422 A1 Jan. 24, 2002

Related U.S. Application Data

(60) Provisional application No. 60/220,372, filed on Jul. 24, 2000.

(51) Int. Cl.[7] .............................. A61K 7/42; A61K 7/00; A01N 25/00
(52) U.S. Cl. .......................... 424/59; 424/401; 424/405
(58) Field of Search ........................... 424/401, 59, 405

(56) References Cited

U.S. PATENT DOCUMENTS

| | | | |
|---|---|---|---|
| 4,348,407 A | 9/1982 | Imondi et al. | |
| RE32,145 E | 5/1986 | Shemano | |
| 4,879,287 A | 11/1989 | Orr et al. | |
| 5,002,938 A | 3/1991 | Wang et al. | |
| 5,110,809 A | 5/1992 | Wang et al. | |
| 5,496,812 A | 3/1996 | Platt | |
| 5,519,059 A | 5/1996 | Sawaya | |
| 5,525,635 A | 6/1996 | Moberg | |
| 5,962,018 A | * 10/1999 | Curtis et al. | 424/450 |
| 6,231,837 B1 | * 5/2001 | Stroud et al. | 424/59 |
| 6,294,186 B1 | * 9/2001 | Beerse et al. | 424/405 |

* cited by examiner

Primary Examiner—Michael G. Hartley
Assistant Examiner—Marina Lamm
(74) Attorney, Agent, or Firm—Linda D. Wheeler, Esq.

(57) ABSTRACT

A combination tanning and antifungal topical system for treating tinea versicolor that includes a body wash, a tanning lotion and anti-fungal topical and a body spray devised to treat tinea versicolor and promote even tanning. The present invention includes the active ingredients tolnaftate and miconazole nitrate.

4 Claims, 2 Drawing Sheets

COMBINATION TANNING AND ANTIFUNGAL TOPICAL SYSTEM FOR TREATING TINEA VERSICOLOR

RELATED APPLICATIONS

This application claims the benefit of U.S. Provisional Patent Application No. 60/220,372 filed on Jul. 24, 2000.

FIELD OF THE INVENTION

The present invention relates generally to tanning products. More specifically, the present invention relates to tanning products that treat tinea versicolor while working to enhance user's tan.

BACKGROUND OF THE INVENTION

Tinea versicolor is an infection of the skin. It generally occurs on the skin of the upper body around the shoulders and upper trunk with the fungus Malasezzia furfur. The fungus de-pigments the skin as it grows and the disease appears as little patches perhaps an eighth to a quarter of an inch in diameter on the affected upper body areas. A tan generally makes the de-pigmentation stand out more making the disease appear to be a disease of the summer months. It is not. Tinea versicolor can occur at any time of the year. It is prominent among tanning bed users. It is caused when fungal spores from the hair fall onto the upper body and germinate on the skin. Once treated, the light areas of the skin will gradually fill back in with normal skin pigment. Various methods and treatments are available to treat the disease, but they are often unpleasant in smell, or leave the skin feeling dry and rough. Accordingly, there is a need for a means by which those who suffer from tinea versicolor can be afforded a method to treat the skin disease in a manner that is quick, easy and effective without being detrimental to the user's skin. The present invention fulfills this need.

SUMMARY OF THE INVENTION

The present invention, combination tanning and antifungal topical system for treating tinea versicolor is a three part system consisting of a body wash, lotion and spray devised to treat tinea versicolor and promote even tanning. The present invention includes the active ingredients tolnaftate, and miconazole nitrate.

It is an object of the present invention to provide a complete treatment system for tinea versicolor.

It is a further object of the present invention to provide a treatment for tinea versicolor that not only eliminates the fungus, but also promotes even tanning.

It is another object of the present invention to provide a complete treatment system for tinea versicolor that is convenient and easy to use.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DETAILED DESCRIPTION OF THE INVENTION

Figure 1:
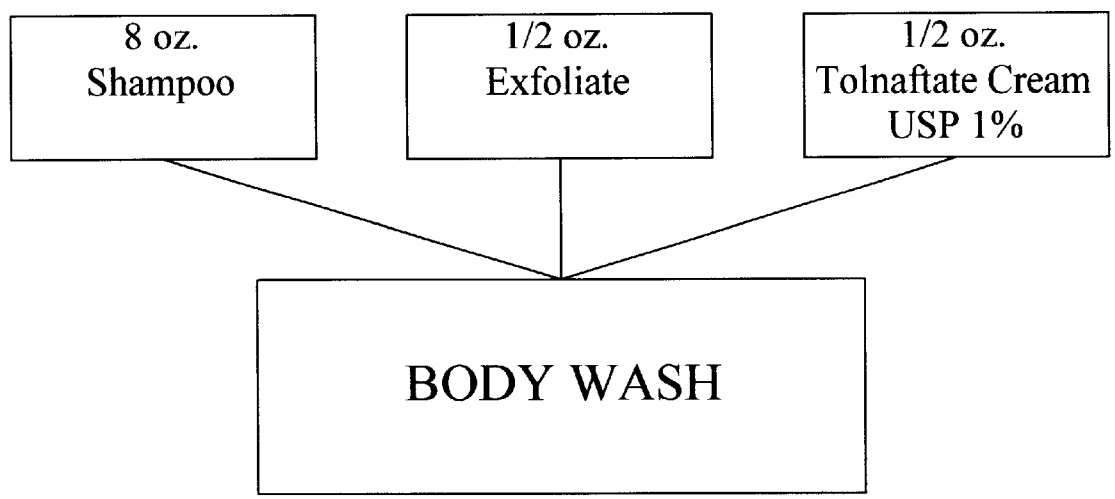
FIG. 1 is a flow chart illustrating which ingredients constitute the body wash.

The present invention, the combination tanning and anti-fungal topical system for treating tinea is a three part system devised to completely treat tinea versicolor. In the preferred embodiment, the first step in using the system is using a body wash. As illustrated in FIG. 1, the preferred embodiment of the body wash of the present invention contains the following major ingredients:

8 oz. Shampoo; minimally containing: water, sodium lauryl sulfate, cocamidopropyl betaine, aloe barbadensis gel, herbal extract, ergocalciferol, corn oil, fragrance, sodium laureth sulfate, tetrasodium edta, ammonium chloride, citric acid, dmdm hydantoin, propylene glycol and color, or their equivalents. One of ordinary skill in the art would recognize that a variety of similar shampoos are already commercially available. One such mixture currently available on the market is Alberto VO5® Herbal Shampoo.

½ oz. Exfoliate; such as walnut shell powder

½ oz. Tolnaftate Cream USP 1%.

Said ingredients are mixed together in random order to form the body wash. One of ordinary skill in the art would readily recognize that the order in which the ingredients are added and mixed together will not affect the effectiveness of the body wash to treat tinea versicolor.

It is preferred that the body wash be used daily by the sufferer. It is further preferred that the body wash be applied during a bath or shower with an exfoliating cloth and that the user's allow the body wash to remain on the body after application for three to five minutes before rinsing. One of ordinary skill in the art would recognize that an exfoliating cloth is not necessary for applying of the body wash. One of ordinary skill in the art would further recognize that the body wash can be made devoid of an exfoliate without altering the intent of the present invention.

Figure 2:
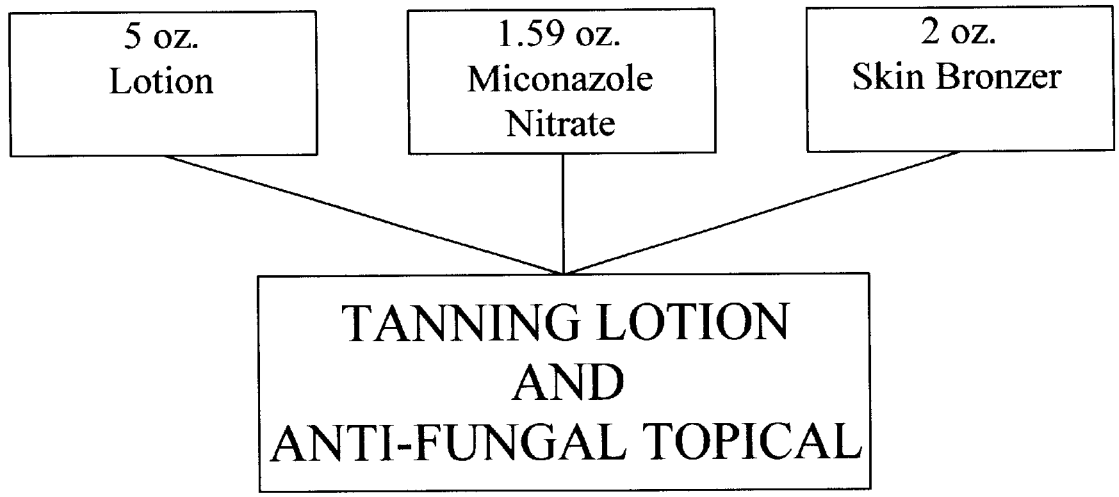
FIG. 2 is a flow chart illustrating which ingredients constitute the tanning lotion and anti-fungal topical.

In the preferred embodiment, step one, application of the body wash, is followed by step two, application of the tanning lotion and anti-fungal topical. As illustrated in FIG. 2, the preferred embodiment of the tanning lotion and anti-fungal topical of the present invention contains the following major ingredients:

5 oz. Lotion; minimally containing: water, glycerine, stearic acid, aloe barbadensis leaf juice, sunflower seed oil, glycol stearate, tea, lecithin pnthenol, tocopheryl acetate, retinyl plaminate, urea, collagen amino acids, sodium lactate, sodium PCA, lactic acid, dimethicone, glyceryl stearate, cetyl alcohol, cetyl phosphate, magnesium aluminum silicate, eucalyptus globulus oil, lavender oil, orange oil, sage oil, gragrance, cabomer, stearamide AMP, corn oil, butylene glycol, methylparaben, DMDM hydantoin, iodopropynyl butlycabamate, disodium EDTA, BHT, color, vitamin E acetate and vitamin A palmitate, or their equivalents. One of ordinary skill in the art would recognize that a variety of similar lotions are already commercially available. Such lotions currently available on the market include Equate® Natural Aloe Lotion and Vaseline® Intensive Care Lotion.

1.59 oz. Miconazole Nitrate 2%

2 oz. Skin Bronzer; One of ordinary skill in the art would recognize that a variety of skin bronzers are already commercially available. Such bronzers currently available on the market include Caymen Sun Secrets® Skin Bronzer.

Said ingredients are mixed together in random order to form the tanning lotion and anti-fungal topical. One of ordinary skill in the art would readily recognize that the order in which the ingredients are added and mixed together will not affect the effectiveness of the tanning lotion and anti-fungal topical to treat tinea versicolor.

In the preferred embodiment, the tanning and anti-fungal topical is used daily. It is applied to user's affected areas directly after use of the body wash and is again applied before the sufferer goes to bed for the night. The tanning lotion and anti-fungal topical works to rid the skin of fungus and infection while restoring color to the affected de-pigmented areas of the skin.

Figure 3:
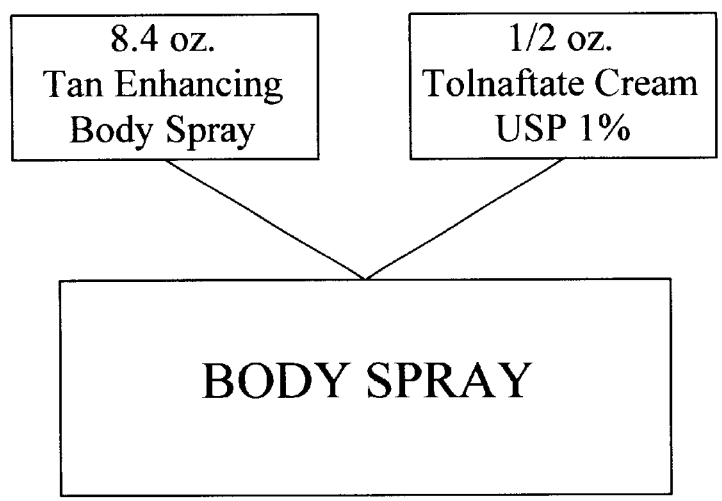
FIG. 3 is a flow chart illustrating which ingredients constitute the body spray.

It is preferred that the third step, the body spray, be applied to user's body after use of a tanning bed or prolonged exposure to the sun. As illustrated in FIG. 3, the preferred embodiment of the body spray of the present invention contains the following major ingredients:

8.4 oz. Tan Enhancing Body Spray; minimally containing: purified water, alcohol SD-40, polysorbate-20, fragrance, glycerin, benzophenone-4 and color, or their equivalents. One of ordinary skill in the art would recognize that a variety of tan enhancing body sprays are already commercially available. Such tan enhancing body sprays currently available on the market include Spa Therapy®.

½ oz. Tolnaftate Cream USP 1%.

Said ingredients are mixed together in random order to form the body spray. One of ordinary skill in the art would readily recognize that the order in which the ingredients are added and mixed together will not affect the effectiveness of the body spray to treat tinea versicolor.

Use of this three step system will work to prevent and treat tinea visicolor.

Although this invention has certain preferred embodiments, it will be obvious to those skilled in the art that various changes and modifications may be made therein without departing from the invention, and all such changes and modifications are intended to fall within the true spirit and scope of the invention.

What is claimed is:

1. A combination tanning and antifungal topical system for treating tinea versicolor, comprising:

a body wash having a mixture of a shampoo and a therapeutically effective amount of tolnaftate cream USP 1%;

a tanning lotion and anti-fungal topical having a mixture of a lotion, a tanning bronzer and a therapeutically effective amount of miconazole nitrate 2%; and, a body spray having a mixture of a liquid tan enhancing body spray and an effective amount of tolnaftate cream 1%.

2. A method for treating tinea versicolor, comprising applying the combination tanning and antifungal topical system of claim 1 to user's skin, wherein the body wash thereof is applied to user's skin with water once per day and then rinsed off and the tanning and anti-fungal topical thereof is applied to the user's skin daily, immediately after use of the body wash and the body spray is applied to user's skin immediately after tanning.

3. The combination tanning and antifungal topical system for treating tinea versicolor;

a body wash having a mixture of a shampoo and an exfoliate and a therapeutically effective amount of tolnaftate cream USP 1%;

a tanning lotion and anti-fungal topical having mixture of a lotion, a tanning bronzer and a therapeutically effective amount of miconazole nitrate 2%; and, a body spray having a mixture of a liquid tan enhancing body spray and an effective amount of tolnaftate cream 1%.

4. A method for treating tinea versicolor, comprising applying the combination tanning and antifungal topical system of claim 3 to user's skin, wherein the body wash thereof is applied to user's skin with water once per day and then rinsed off and the tanning lotion and anti-fungal topical thereof is applied to the user's skin daily, immediately after use of the body wash and the body spray thereof is applied to user's skin immediately after tanning.

* * * * *